United States Patent
Yeon et al.

(10) Patent No.: US 9,579,634 B2
(45) Date of Patent: Feb. 28, 2017

(54) METHOD FOR PRODUCING METAL CATALYST FOR PREPARING ALCOHOL AND METAL CATALYST PRODUCED THEREBY

(71) Applicant: Korea Institute of Energy Research, Daejeon (KR)

(72) Inventors: Sun-Hwa Yeon, Daejeon (KR); Dae-Hyun Shin, Daejeon (KR); Nam-Sun Nho, Daejeon (KR); Kyoung-Hee Shin, Daejeon (KR); Chang-Soo Jin, Daejeon (KR); Sung-Chan Nam, Daejeon (KR); Je-Kyoung Woo, Daejeon (KR); Kwang-Ho Kim, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 609 days.

(21) Appl. No.: 14/049,019

(22) Filed: Oct. 8, 2013

(65) Prior Publication Data
US 2014/0106959 A1   Apr. 17, 2014

(30) Foreign Application Priority Data
Oct. 10, 2012   (KR) ......................... 10-2012-0112179

(51) Int. Cl.
| | |
|---|---|
| B01J 23/70 | (2006.01) |
| B01J 23/72 | (2006.01) |
| B01J 37/34 | (2006.01) |
| B01J 21/06 | (2006.01) |
| B01J 21/18 | (2006.01) |
| B01J 23/04 | (2006.01) |

(Continued)

(52) U.S. Cl.
CPC ............... *B01J 23/72* (2013.01); *B01J 21/063* (2013.01); *B01J 21/18* (2013.01); *B01J 23/04* (2013.01); *B01J 23/28* (2013.01); *B01J 23/34* (2013.01); *B01J 23/745* (2013.01); *B01J 23/75* (2013.01); *B01J 23/80* (2013.01); *B01J 37/0201* (2013.01); *B01J 37/34* (2013.01); *C07C 29/154* (2013.01); *Y02P 20/52* (2015.11)

(58) Field of Classification Search
USPC ....................................................... 502/345
See application file for complete search history.

(56) References Cited

U.S. PATENT DOCUMENTS

| | | | |
|---|---|---|---|
| 8,623,927 B2 | 1/2014 | Kang et al. | |
| 2008/0277844 A1* | 11/2008 | Chai | B22F 3/003 266/275 |
| 2011/0288353 A1* | 11/2011 | Dai | C10G 49/02 585/250 |

FOREIGN PATENT DOCUMENTS

| | | |
|---|---|---|
| KR | 1020080108605 A | 12/2008 |
| KR | 1020100011957 A | 2/2010 |

(Continued)

*Primary Examiner* — Melvin C Mayes
*Assistant Examiner* — Kenneth Vaden
(74) *Attorney, Agent, or Firm* — Amanda M. Prose; Westman, Champlin & Koehler, P.A.

(57) ABSTRACT

Disclosed is a method for preparing a metal catalyst having improved yield of alcohols. The method for preparing a metal catalyst for the production of alcohol from synthesis gas includes forming a metal catalyst; and irradiating the metal catalyst with gamma rays. The metal catalyst has improved yield of alcohols by stabilizing the metal catalyst through gamma ray irradiation to inhibit generation of hydrocarbons in catalytic reaction with synthesis gas.

7 Claims, 8 Drawing Sheets

(51) Int. Cl.
*B01J 23/28* (2006.01)
*B01J 23/34* (2006.01)
*B01J 23/745* (2006.01)
*B01J 23/75* (2006.01)
*B01J 23/80* (2006.01)
*B01J 37/02* (2006.01)
*C07C 29/154* (2006.01)

(56) References Cited

FOREIGN PATENT DOCUMENTS

| KR | 1020100024169 A | 3/2010 |
|----|-----------------|--------|
| WO | 2007117590 A2 | 10/2007 |

* cited by examiner

METHOD FOR PRODUCING METAL CATALYST FOR PREPARING ALCOHOL AND METAL CATALYST PRODUCED THEREBY

CROSS-REFERENCE TO RELATED APPLICATIONS

This application claims the benefit of Korean Patent Application No. 10-2012-0112179, filed with the Korean Intellectual Property Office on Oct. 10, 2012, the disclosure of which is incorporated herein by reference in its entirety.

BACKGROUND

1. Technical Field

The present invention relates to a method for producing a metal catalyst for preparing alcohols through catalytic reaction, and more particularly, to a method for producing a metal catalyst for catalyzing conversion of synthetic gas into alcohols.

2. Description of the Related Art

Generally, "synthesis gas (synthesis gas)" refers to a gas mixture containing various amounts of carbon oxides (like carbon monoxide) and hydrogen. Such a term comes from its use as an intermediate in production of synthetic natural gas, ammonia, alcohols or other fuels.

Synthesis gas may be produced in various ways, for example, by gasification of carbon-containing fuels into products in a gas phase having heating value, for instance, by gasification of coal, biomass or municipal waste. Further, the synthesis gas may be produced by steam reforming of natural gas, methane from various sources, or liquid hydrocarbons. The synthesis gas is combustible and may be used as a fuel source or an intermediate for production of other chemical materials. The synthesis gas may also be used as an intermediate in producing synthetic petroleum for use as fuel or lubricant via catalytic reaction a Fischer-Tropsch catalyst.

Worldwide energy consumption has been continuously increasing, and greatly relies on fossil fuels such as petroleum, natural gas, and coal. However, fossil fuel reserves are considerably limited and consumption of fossil fuels is greatly exceeding production. Given such a circumstance, there is strong demand for a new energy source capable of effectively replacing fossil fuels. Renewable fuels such as alcohols, particularly ethanol, draw considerable attention as a hydrogen source for automobiles, chemical additives or fuel cells.

Specifically, fuel cells convert chemical energy into electric energy through electrochemical reaction of oxygen and hydrogen. Since fuel batteries are characterized by having high energy utilization efficiency, studies into practical application have been actively conducted for the purpose of public welfare, industries, automobiles, and the like.

As methods for producing an alcohol from synthesis gas for use as a raw material for fuel cells, technology using a catalyst, specifically a metal catalyst, is well known and considerable research thereon has been carried out. In research of catalysts, the most important goal, in terms of fundamental function of a metal catalyst, is improvement in catalyst performance. In order to efficiently perform catalysis, a promoter, a support, or the like of the catalyst may be redesigned.

As a representative metal catalyst for synthesizing an alcohol including ethanol using synthetic gas, Cu catalyst is used. However, the Cu catalyst has a demerit in that alcohol yield is low due to co-production of hydrocarbons during alcohol synthesis.

[Prior Art Document] KR 10-2008-0108605 A

BRIEF SUMMARY

The present invention has been conceived to solve problems in the art and an object of the present invention is to provide a method for producing a metal catalyst improving alcohol yield.

In accordance with one aspect of the present invention, a method for producing a metal catalyst for the preparation of an alcohol from synthesis gas includes: forming a metal catalyst; and irradiating the metal catalyst with gamma rays.

The present inventors developed a method for producing a metal catalyst capable of reducing generation of hydrocarbons by employing a method for stabilizing a metal catalyst by irradiating the metal catalyst with gamma rays and changing electron value of the metal catalyst to 0, thereby inhibiting side reaction during catalytic reaction with synthesis gas.

The gamma rays may have an intensity of 20 kGy to 100 kGy and may be irradiated for 1 hour to 2 hours.

The metal catalyst may be prepared using at least one selected from Cu, Li, Co, Fe, Mo, and Mn. The operation of forming a metal catalyst may include: (1-1) dissolving a precursor material of the metal catalyst in distilled water; (1-2) preparing a slurry by mixing the precursor material with a catalyst support; and (1-3) sintering the slurry after drying.

In the case that Cu is used as the metal, the precursor material may be selected from copper nitrate hydrates, copper sulfate hydrates, and copper phosphate hydrates, and the like. The catalyst support may include at least one selected from the group consisting of activated carbon, ZnO, $TiO_2$, zeolite and MoF (metal organic framework). The amount of the metal on the catalyst support may range from 3 wt % to 10 wt %.

According to another aspect of the present invention, a metal catalyst used for preparation of an alcohol from synthesis gas is prepared by the aforementioned method according to the present invention.

According to a further aspect of the present invention, a method for producing an alcohol from synthesis gas includes: providing a metal catalyst prepared by the aforementioned method; reacting the metal catalyst with synthesis gas; and collecting alcohol from the reacted gases, wherein the metal catalyst irradiated with gamma rays is subjected to catalytic reaction to inhibit generation of hydrocarbons.

As such, the present invention may provide a metal catalyst having improved yield of alcohol by stabilizing the metal catalyst through gamma irradiation to inhibit generation of hydrocarbons in catalytic reaction with synthesis gas.

BRIEF DESCRIPTION OF DRAWINGS

The above and other aspects, features and advantages of the present invention will become apparent from the following description of embodiments given in conjunction with the accompanying drawings, in which.

DETAILED DESCRIPTION

Embodiments of the present invention will now be described with reference to the accompanying drawings.

Catalyst Synthesis

In one example, a Cu catalyst was prepared by incipient wetness impregnation.

As a copper precursor of a metal catalyst, copper (II) nitrate trihydrate (Junsei Chemical Co., Ltd.) was used. As a catalyst support, activated carbon, ZnO and $TiO_2$ were used.

1.2 g of copper (II) nitrate trihydrate $(CuNO_3)_2 \cdot 3H_2O$ was dissolved in 6 ml of distilled water. The resulting solution was added dropwise to 6 g of three kinds of supports and mixed to form a slurry.

The prepared slurry was dried at 373K and sintered at 673K for 4 hours to prepare a Cu catalyst supported on the support.

Subsequently, the Cu catalyst, in which 5 wt % of Cu was supported on the support, was placed in a vial and irradiated with 20 kGy of gamma rays for 1 hour. When a metal catalyst supported on a porous matrix is irradiated with gamma rays, electrovalence of a metal ion was changed to 0 to stabilize the metal, thereby preventing side reaction due to hydrocarbons during catalysis reaction.

In a comparative example, a Cu catalyst was prepared without irradiation with gamma rays.

Preparation of Alcohol

The catalyst prepared according to the above method was used to produce an alcohol from synthesis gas using a fixed-bed channel reactor which has an inner diameter of 8 mm and a length of 450 mm. The prepared alcohol was evaluated as to various properties.

1 g of each of the catalysts prepared in the example and the comparative example was placed in the middle of the reactor, followed by packing the catalyst with silica wool in order to prevent migration of the catalyst due to gas flux.

First, in order to activate the catalyst, the catalyst was reduced by feeding a gas mixture of $H_2$ and Ar in a volume ratio of 1:9 was fed at 673K for 2 hours at a flux of 20 cm$^3$/min, as measured at standard temperature and pressure (STP).

After reducing the catalyst, synthesis gas comprised of $H_2$ and CO mixed in a volume ratio of 2:1 was used in catalytic reaction to prepare an alcohol under conditions of a gas space velocity (GHSV) of 600 cm$^3$/($V_{cat}$·h) to 2400 cm$^3$/($V_{cat}$·h), a temperature of 473K to 573K, a total pressure of 20 atm to 30 atm, and a gas flux of 100 cm$^3$/min to 400 cm$^3$/min, as measured at standard temperature and pressure (STP).

Two thermocouples were placed above and below the catalyst in the reactor, and the temperature sensed through the thermocouples was maintained within the range of ±2K.

A high temperature gas discharged from the reactor through from the catalytic reaction was passed through a chiller at −10° C. to collect a liquid product, and unreacted $H_2$ and CO gases were discharged.

Such catalytic reaction was performed for 5 hours and the collected liquid product was analyzed.

Figure 1:
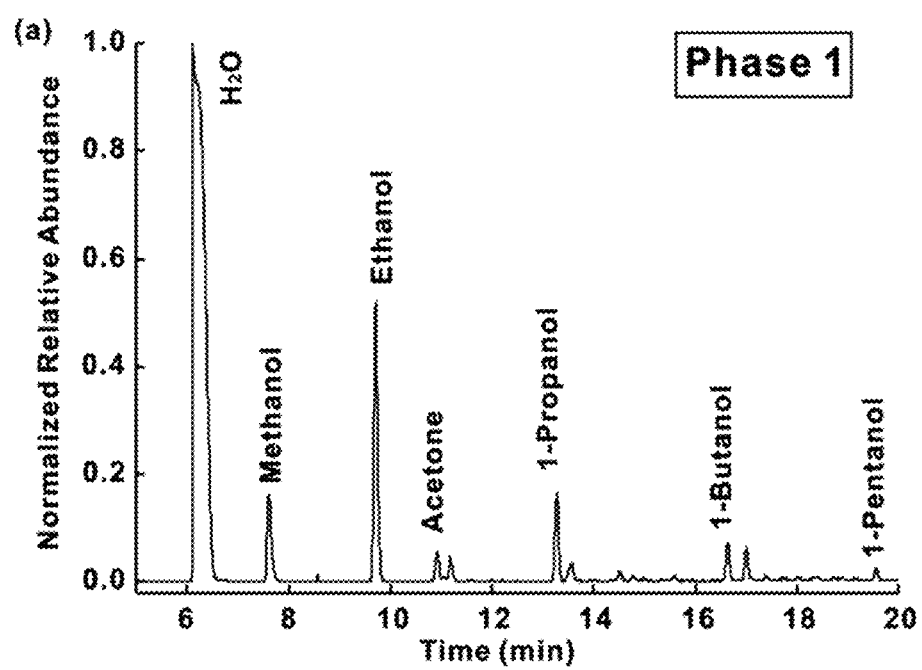
FIGS. 1 to 3 show results of GCMSS analysis of a product prepared using a catalyst supported on activated carbon in a comparative example.
Figure 2:
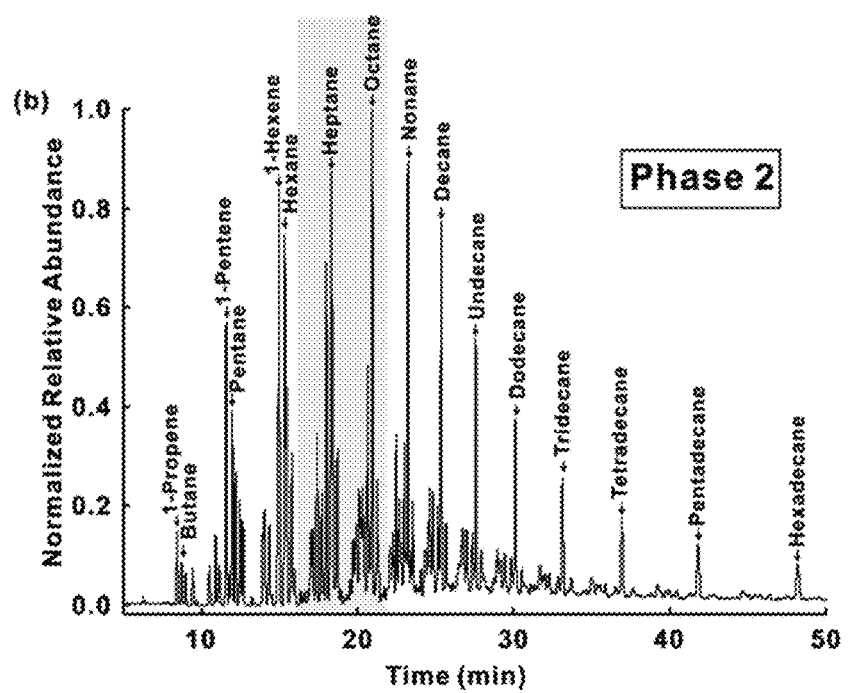
Figure 3:
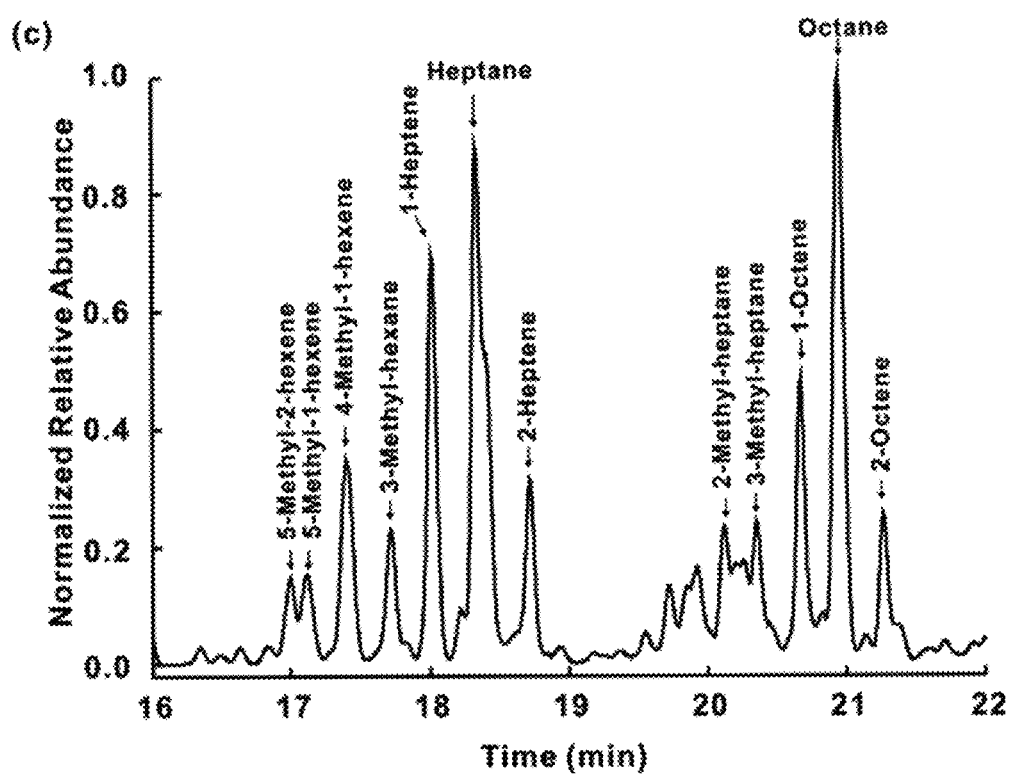

FIGS. 1 to 3 show results of GCMSS analysis of a product prepared using the catalyst having an activated carbon support in one comparative example. In catalytic reaction, the temperature was 300° C., the pressure was 30 bar, and GHSV was 1800 h$^{-1}$.

The product obtained by catalytic reaction with a Cu catalyst supported on activated carbon and not irradiated with gamma rays in the comparative example had two phases, as depicted in FIGS. 1 and 2.

Phase 1 depicted in FIG. 1 shows alcohols such as methanol, ethanol, and the like besides water. Phase 2 depicted in FIG. 2 shows hydrocarbons. FIG. 3 shows an enlarged view of the portion where components appeared densely in FIG. 2.

Analysis results of FIGS. 1 to 3 are shown in Table 1.

TABLE 1

| | Component | Retention Time(min) | Compositions (%) | |
|---|---|---|---|---|
| Phase 1 | $H_2O$ | 6.14 | 75.577 | 60.456 |
| | Methanol | 7.598 | 3.597 | 2.8776 |
| | Ethanol | 9.72 | 9.968 | 7.96 |
| | 1-Propanol | 13.27 | 2.881 | 2.3 |
| | 1-Butanol | 16.66 | 1.222 | 0.976 |
| | 1-Pentanol | 19.56 | 0.352 | 0.416 |
| | Others | — | 6.755 | 5.404 |
| | Sum | | 100 | 80 |
| Phase 2 | Hydrocarbon Sum | — | 100 | 20 |
| Sum | | | | 100 |

The product prepared using the catalyst having an activated carbon support in the comparative example was comprised of 80% of alcohols and 20% of hydrocarbons. The alcohols were mainly comprised of ethanol and methanol.

Figure 4:
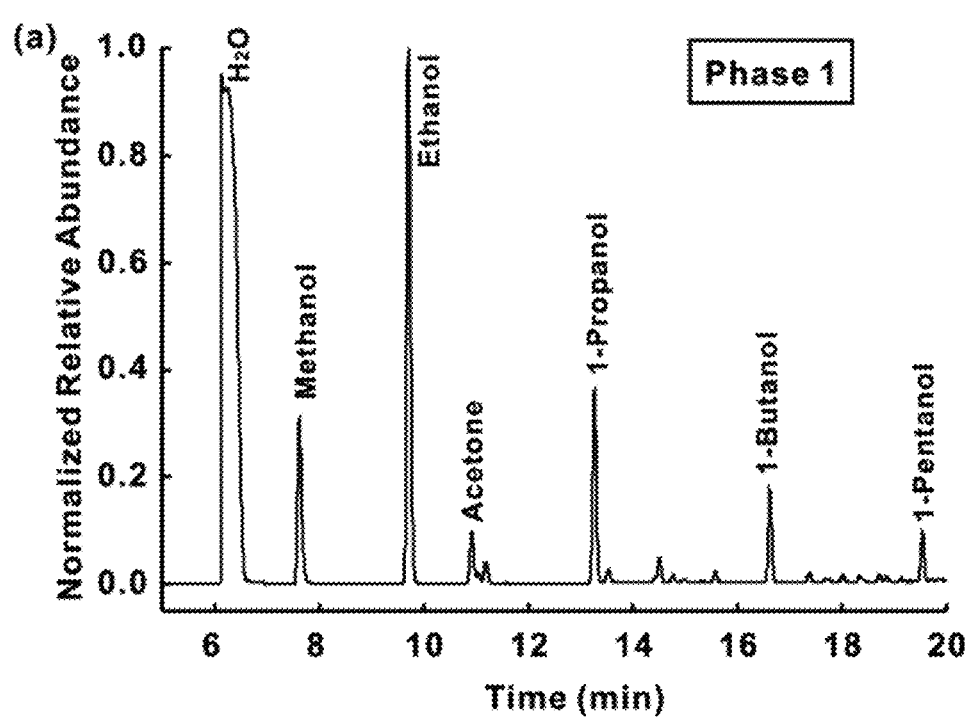
FIGS. 4 to 6 show results of GCMSS analysis of a product prepared using a catalyst supported on $TiO_2$ in a comparative example.
Figure 5:
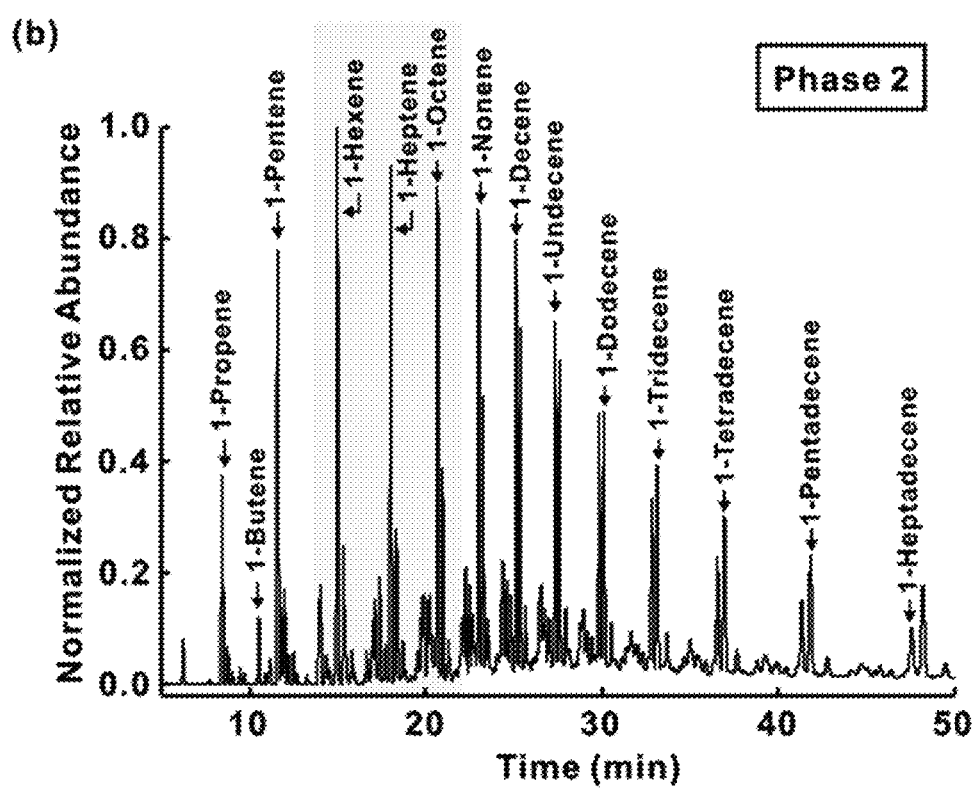
Figure 6:
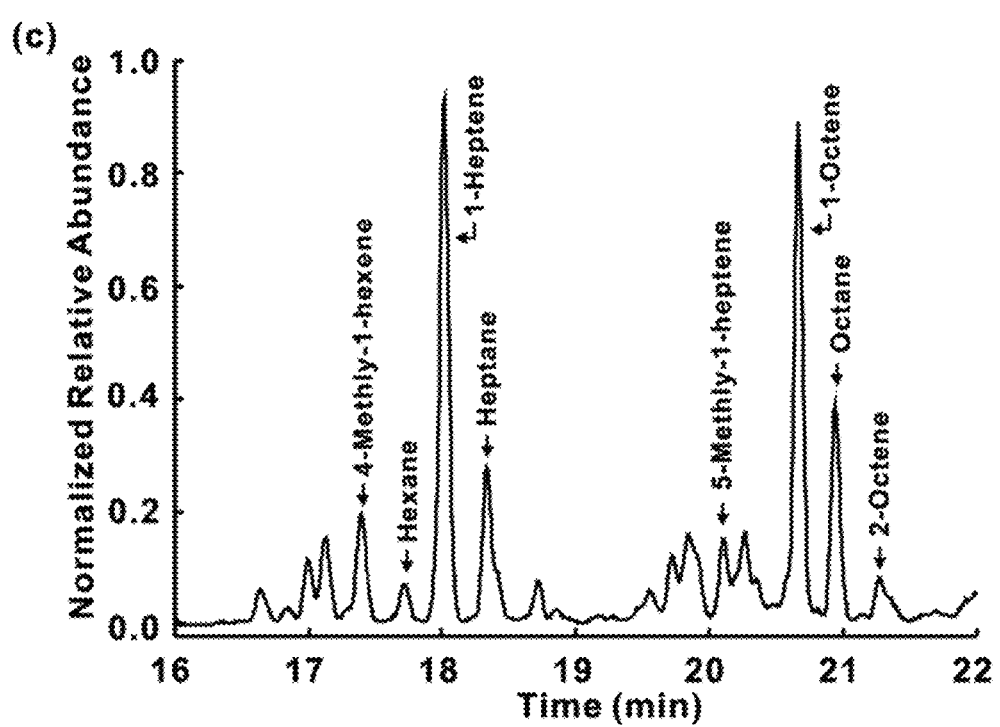

FIGS. 4 to 6 show results of GCMSS analysis of a product prepared using a catalyst having a $TiO_2$ support in another comparative example. In catalytic reaction, the temperature was 300° C., the pressure was 30 bar, and GHSV was 2400 h$^{-1}$.

The product prepared by catalytic reaction with a Cu catalyst supported on $TiO_2$ and not irradiated with gamma rays in this comparative example had two phases as depicted in FIGS. 4 and 5.

Phase 1 depicted in FIG. 4 shows alcohols such as methanol, ethanol, and the like besides water. Phase 2 depicted in FIG. 5 shows hydrocarbons. FIG. 6 shows an enlarged view of the portion where components appeared densely in FIG. 5.

The analysis results of FIGS. 4 to 6 are shown in Table 2.

TABLE 2

| | Component | Retention Time(min) | Compositions (%) | |
|---|---|---|---|---|
| Phase 1 | $H_2O$ | 6.14 | 66 | 46.2 |
| | Methanol | 7.598 | 8.4 | 5.9 |
| | Ethanol | 9.72 | 13.0 | 9.1 |
| | 1-Propanol | 13.27 | 4.47 | 3.1 |

TABLE 2-continued

| | Component | Retention Time(min) | Compositions (%) | |
|---|---|---|---|---|
| | 1-Butanol | 16.66 | 1.9 | 1.3 |
| | 1-Pentanol | 19.56 | 0.8 | 0.6 |
| | Others | — | 5.3 | 3.7 |
| | Sum | | 100 | 70 |
| Phase 2 | Hydrocarbon Sum | — | 100 | 30 |
| Sum | | | | 100 |

The product prepared using the catalyst supported on $TiO_2$ in this comparative example was comprised of 70% of alcohols and 30% of hydrocarbons. The alcohols were mainly comprised of ethanol and methanol.

As can be seen from the above, it was observed that, when a Cu catalyst of the related art, which was not irradiated with gamma rays, was catalytically reacted with synthesis gas, hydrocarbons were prepared together with alcohols.

Figure 7:
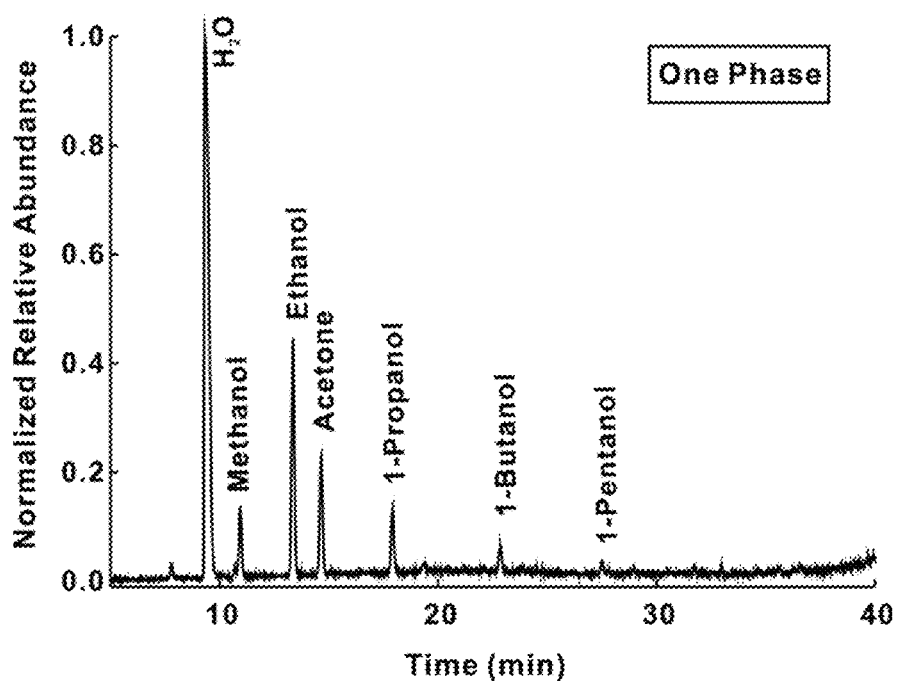
FIG. 7 shows a result of GCMSS analysis of a product prepared using a catalyst supported on activated carbon in one example of the present invention.

FIG. 7 shows a result of GCMSS analysis of a product prepared using a catalyst having an activated carbon support in one example of the present invention. In catalytic reaction, the temperature was 300° C., the pressure was 30 bar, and GHSV was 2300 $h^{-1}$.

The product prepared by catalytic reaction with the Cu catalyst supported on activated carbon and irradiated with 20 kGy of gamma rays in this example had a single phase (one phase) as depicted in FIG. 7. The components included in a single phase were alcohols such as methanol and ethanol and the like besides water.

The analysis results of FIG. 7 are shown in Table 3.

TABLE 3

| Component | Retention Time (min) | Compositions (%) |
|---|---|---|
| $H_2O$ | 9.332 | 61.2 |
| Methanol | 10.948 | 4.7 |
| Ethanol | 13.353 | 16.4 |
| Acetone | 14.647 | 8.5 |
| 1-Propanol | 17.914 | 4.6 |
| 1-Butanol | 22.844 | 2.0 |
| 1-Pentanol | 27.524 | 0.8 |
| Others | — | 1.9 |

It can be seen that the product prepared using the Cu catalyst having the activated carbon support in the example of the present invention did not contain hydrocarbons, and the amounts of methanol and ethanol were increased as compared to Table 1.

Figure 8:
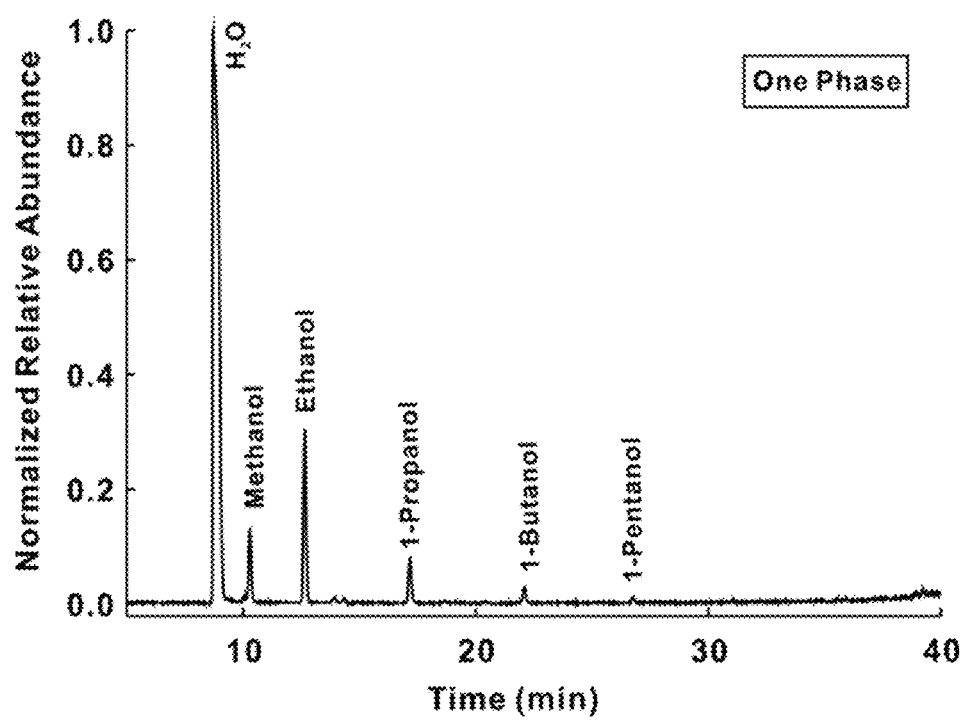
FIG. 8 shows a result of GCMSS analysis of a product prepared using the catalyst supported on ZnO in another example of the present invention.

FIG. 8 shows a result of GCMSS analysis of a product prepared using a catalyst having a ZnO support according to another example of the present invention. In catalytic reaction, the temperature was 300° C., the pressure was 30 bar, and GHSV was 1800 $h^{-1}$.

The product prepared by catalytic reaction with the Cu catalyst supported on ZnO and irradiated with 20 kGy of gamma rays in this example had a single phase as depicted in FIG. 8. The components included in a single phase were alcohols such as methanol and ethanol besides water.

The analysis results of FIG. 8 are shown in Table 4.

TABLE 4

| Component | Retention Time (min) | Compositions (%) |
|---|---|---|
| $H_2O$ | 8.71 | 75 |
| Methanol | 10.3 | 4.28 |
| Ethanol | 12.66 | 10.589 |
| 1-Propanol | 17.1 | 2.94 |
| 1-Butanol | 22.1 | 10.9 |
| 1-Pentanol | 26.8 | — |
| Others | — | 4.99 |

It can be seen that the product prepared using the catalyst having the ZnO support in this example of the present invention did not contain hydrocarbons.

As such, it can be seen that, when synthesis gas was subjected to catalytic reaction using a Cu catalyst prepared by irradiating gamma rays in this example, hydrocarbons were not prepared and only water and alcohols were prepared.

In conclusion, the Cu catalyst prepared by irradiating gamma rays inhibits formation of hydrocarbons during catalytic reaction with synthesis gas, thereby preparing a product comprised of mixed alcohols. In this case, there is a merit in that the process of separating hydrocarbons and alcohols in the product of catalytic reaction can be omitted.

Although some embodiments have been provided to illustrate the present invention, it should be understood that these embodiments are given by way of illustration only, and that various modifications, variations, and alterations can be made without departing from the spirit and scope of the present invention. The scope of the present invention should be limited only by the accompanying claims and equivalents thereof.

What is claimed is:

1. A method for producing a metal catalyst for the preparation of alcohols from synthesis gas, comprising:
    forming a metal catalyst; and
    irradiating the metal catalyst with gamma rays to stabilize the electrovalence of the metal in the catalyst and to inhibit side reactions when the metal catalyst is subjected to catalytic reaction with the synthesis gas, and
    wherein the metal catalyst is prepared using at least one selected from Cu, Li, Co, Fe, Mo, and Mn.

2. The method according to claim 1, wherein the gamma rays have an intensity of 20 kGy to 100 kGy.

3. The method according to claim 2, wherein the gamma rays are irradiated for 1 hour to 2 hours.

4. The method according to claim 3, wherein the forming a metal catalyst comprises:
    dissolving a precursor material of the metal catalyst in distilled water;
    preparing a slurry by mixing the precursor material with a catalyst support; and
    sintering the slurry after drying.

5. The method according to claim 4, wherein the precursor material is at least one selected from copper nitrate hydrates, copper sulfate hydrates, and copper phosphate hydrates.

6. The method according to claim 4, wherein the catalyst support is at least one selected from the group consisting of activated carbon, ZnO, $TiO_2$, zeolite and MoF (metal organic framework).

7. The method according to claim 4, wherein the amount of metal supported on the catalyst support ranges from 3 wt % to 10 wt %.

* * * * *